United States Patent [19]
Kim

[11] Patent Number: 5,868,787
[45] Date of Patent: Feb. 9, 1999

[54] ORTHODONTIC TWEEZERS WITH A GAUGE

[76] Inventor: Joong Han Kim, 1691-8, Seocho 1-Dong, Seocho-Gu, Seoul, Rep. of Korea

[21] Appl. No.: 735,737

[22] Filed: Oct. 23, 1996

[30] Foreign Application Priority Data

Oct. 23, 1995 [KR] Rep. of Korea ................. 1995-36684

[51] Int. Cl.[6] .................................................. A61B 17/50
[52] U.S. Cl. .......................................... 606/211; 606/210
[58] Field of Search ................................... 606/211, 210, 606/205, 208, 206

[56] References Cited

U.S. PATENT DOCUMENTS

| | | | |
|---|---|---|---|
| 5,385,471 | 1/1995 | Chuen | 606/210 |
| 5,520,704 | 5/1996 | Castro et al. | 606/210 |

*Primary Examiner*—Michael Buiz
*Assistant Examiner*—Kevin Truong
*Attorney, Agent, or Firm*—Oliff & Berridge

[57] ABSTRACT

The present invention provides tweezers with a guage for holding and affixing the bracket accurately and precisely to the patient's tooth. Also, the present invention provides tweezers with a guage suitable for minimizing the operator's working time and difficulty. Therefore, there are provided tweezers comprising a pair of generally flat elongated members placed in an adjacent lengthwise relationship with one another, each member having a first end part and a second end part, the second end forming a gripping jaw which has a groove at the central section of its front surface; means for adjusting the bracket positioned between the members and extending along the longitudinal direction of the tweezers, said means for adjusting the bracket, including one end portion connected with the first end parts of the members and the other end portion formed as an adjustment plate extending along the groove of the gripping jaw, for accurately adjusting the position of the bracket and forming a reference point to measure distance when the adjustment plate is inserted into a slot of the bracket; and means for measuring distance between the end of tooth and a slot of the bracket, including a pivoting shaft and a number of plates which are stacked on each other and associated with at least one surface of the means for adjusting the bracket by the pivoting shaft.

8 Claims, 12 Drawing Sheets

ORTHODONTIC TWEEZERS WITH A GAUGE

BACKGROUND OF THE INVENTION

The present invention relates to orthodontic tweezers used for affixing brackets to a patient's tooth, and more particularly to orthodontic tweezers with a gauge used for affixing and holding brackets precisely and accurately to the attaching position of the patient's tooth.

Figure 1:
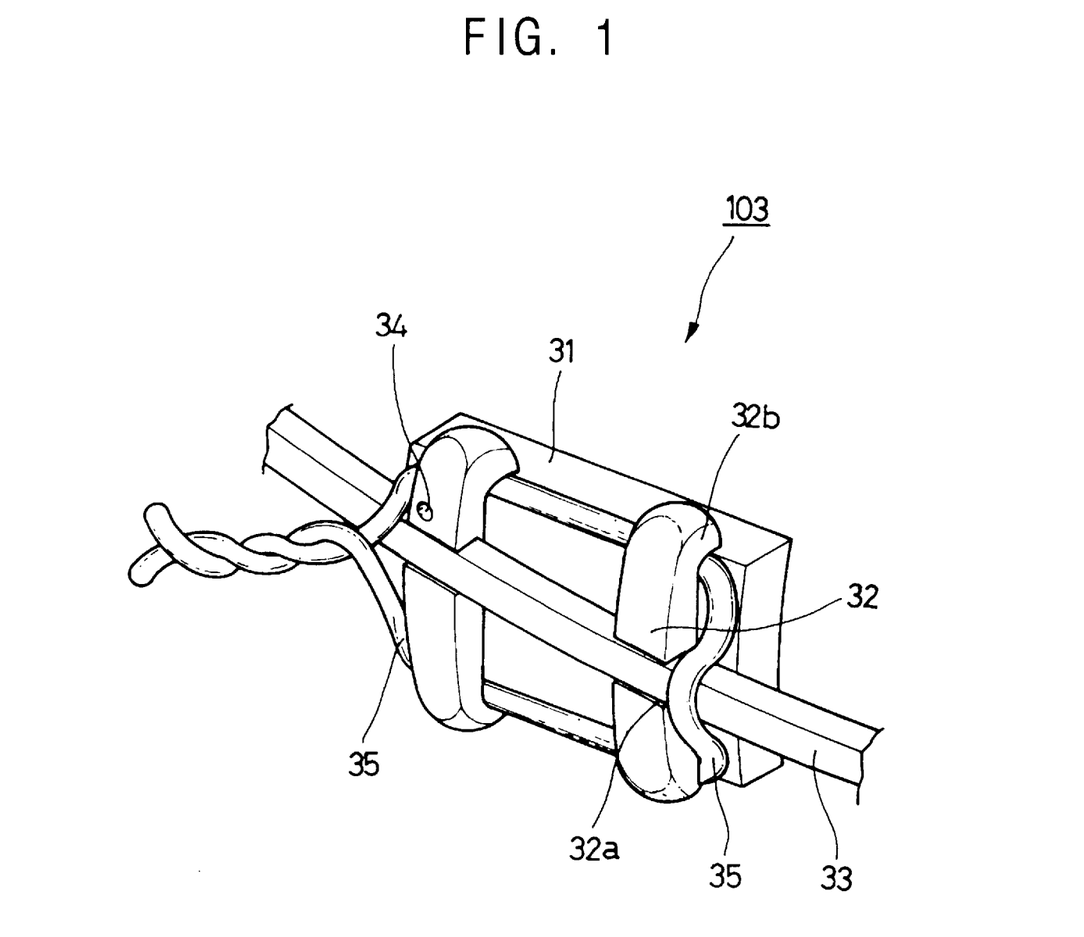
FIG. 1 is a perspective view of a bracket associated with a ligature wire and an archwire.

There are two types of orthodontic brackets. The first is an anterior bracket, designed for attachment to front teeth and the second is a posterior bracket, designed for attachment to back teeth. Generally, as can be seen in FIG. 1 and FIG. 2A, an orthodontic bracket is comprised of a base 31, a slot 32a, an identification mark 34, and a stem 36 having tie wing 32b.

The base 31 is slightly larger than the center section of the bracket 103 and is concave to conform to the surface of the patient's tooth. The chamfered slot 32a is slightly angled to the horizontal center line of the bracket 103 to receive an archwire 33 which makes an ideal dentition. The tie wing 32b, being of rhomboidal construction, is used for securing the labial tooth surface's not coming in contact with a ligature wire 35. The identification mark allows an orthodontist quicker identification when rebonding a loose bracket. The ligature wire 35 holds the archwire 33 which will make the ideal dentition after the bracket 103 is glued to the patient's tooth. The stem 36 is integrally formed on the base 31 in order to receive the ligature wire 35 or an elastic ligature.

To make a functional dentition, the orthodontist must glue the bracket 103 accurately 3.5 mm~5 mm away from the end of the tooth and rapidly onto the surface of the tooth, because orthodontic bonding materials are congealed within 30 seconds. Simultaneously, the orthodontist must glue the bracket 103 parallel to the vertical axis of the tooth, referring to a vertical scribe line (not shown) of the bracket 103.

Figure 2A:
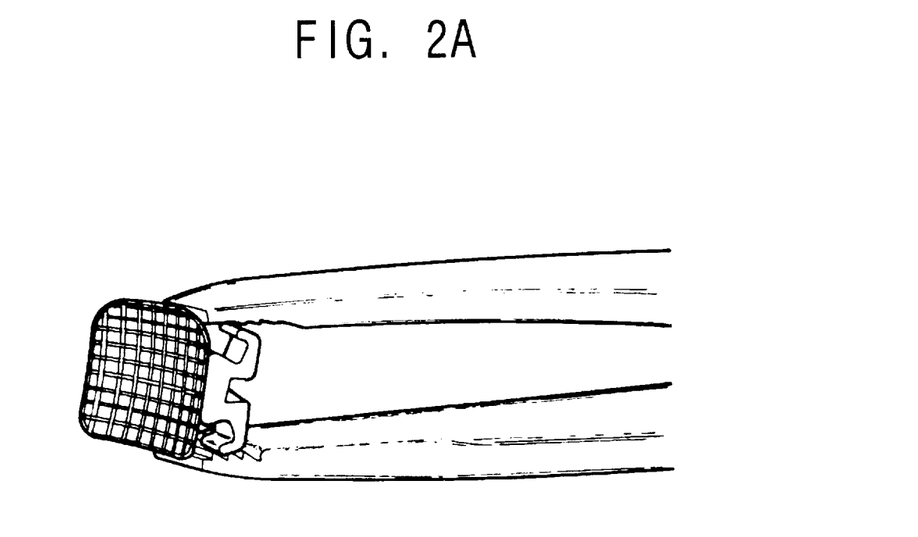
FIG. 2A is a perspective view of non-tensioned tweezers according to the prior art holding an anterior bracket.
Figure 2B:
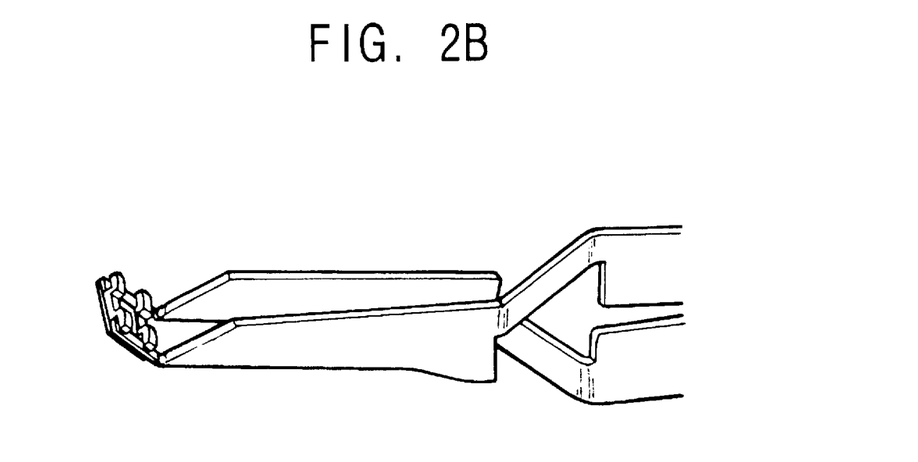
FIG. 2B is a perspective view of pretensioned tweezers according to the prior art holding a posterior bracket.

Orthodontic tweezers in accordance with the prior art are generally either of the pretentioned or cross-over type, or the non-tensioned type as can be seen in FIG. 2A and FIG. 2B. The non-tensioned tweezer has a gripping jaw which is not normally in the closed position, but rather must be closed by its user. The cross-over type, on the other hand, has a gripping jaw which is held in the closed position by tension formed by the shape of the tweezer. The user must apply pressure to the members to open the jaw, align the object upon which the tweezers are to be used with, and then reduce the pressure on the members so that the object is held by the gripping area.

The cross-over type is preferred over other designs for work requiring the object to be held securely and accurately, as the amount of force used to hold the object does not depend on the amount of pressure applied by the user. This is especially crucial in the orthodontics field and in the placement of brackets on the patient's teeth, because such brackets are very small and must be held securely and located precisely. Therefore, the preferred embodiment of the tweezers in accordance with this invention uses the cross-over design. However, this invention is not limited to such tweezers, and could also embody tweezers which are not the cross-over type.

On the other hand, to attach the bracket to the patient's tooth, the orthodontist generally uses various conventional tweezers for gripping the bracket. Also, to measure distance between the end of tooth and the bracket the orthodontist generally uses a gauge comprising four different measurement parts which allow the dentist to select the right height for any tooth or uses the naked eye. Using one or both of these methods, the orthodontist ascertains whether or not the bracket is in an accurate position.

However, the prior art system for attaching brackets discussed has limitations in that the bracket is sometimes not in an accurate and precise position and it takes the orthodontist a lot of time to attach the bracket.

The present invention provides tweezers with a guage which overcomes the above mentioned limitations of the prior art system for attaching the bracket. Tweezers with a guage according to the present invention can help the user attach the brackets more accurately and precisely to the patient's tooth and will serve well in the orthodontic field. Also, the user, using the tweezers according to its designated purpose, can more quickly attach the bracket to the patient's tooth with greater comfort.

SUMMARY OF THE INVENTION

It is a purpose of the present invention to provide tweezers with a guage for holding and affixing the bracket accurately and precisely to the patient's teeth.

It is another purpose of the present invention to provide tweezers with a guage suitable for minimizing the operator's working time and difficulty. To achieve the above purposes, there are provided tweezers comprising a pair of generally flat elongated members placed in an adjacent lengthwise relationship with one another, each member having a first end part and a second end part, the second end forming a gripping jaw which has a groove at the central section of its front surface; means for adjusting the bracket positioned between the members and extending along the longitudinal direction of the tweezers, said means for adjusting the bracket, including one end portion connected with the first end parts of the members and the other end portion formed as an adjustment plate extending along the groove of the gripping jaw, for accurately adjusting the position of the bracket and forming a reference point to measure distance when the adjustment plate is inserted into a slot of the bracket; and means for measuring distance between the end of tooth and a slot of the bracket, including a pivoting shaft and a number of plates which are stacked on each other and associated with at least one surface of the means for adjusting the bracket by the pivoting shaft.

DETAILED DESCRIPTION OF THE INVENTION

The above purposes and advantages of the present invention will become more apparent by the detailed description of preferred embodiments below and by referring to the attached drawings.

Figure 3A:
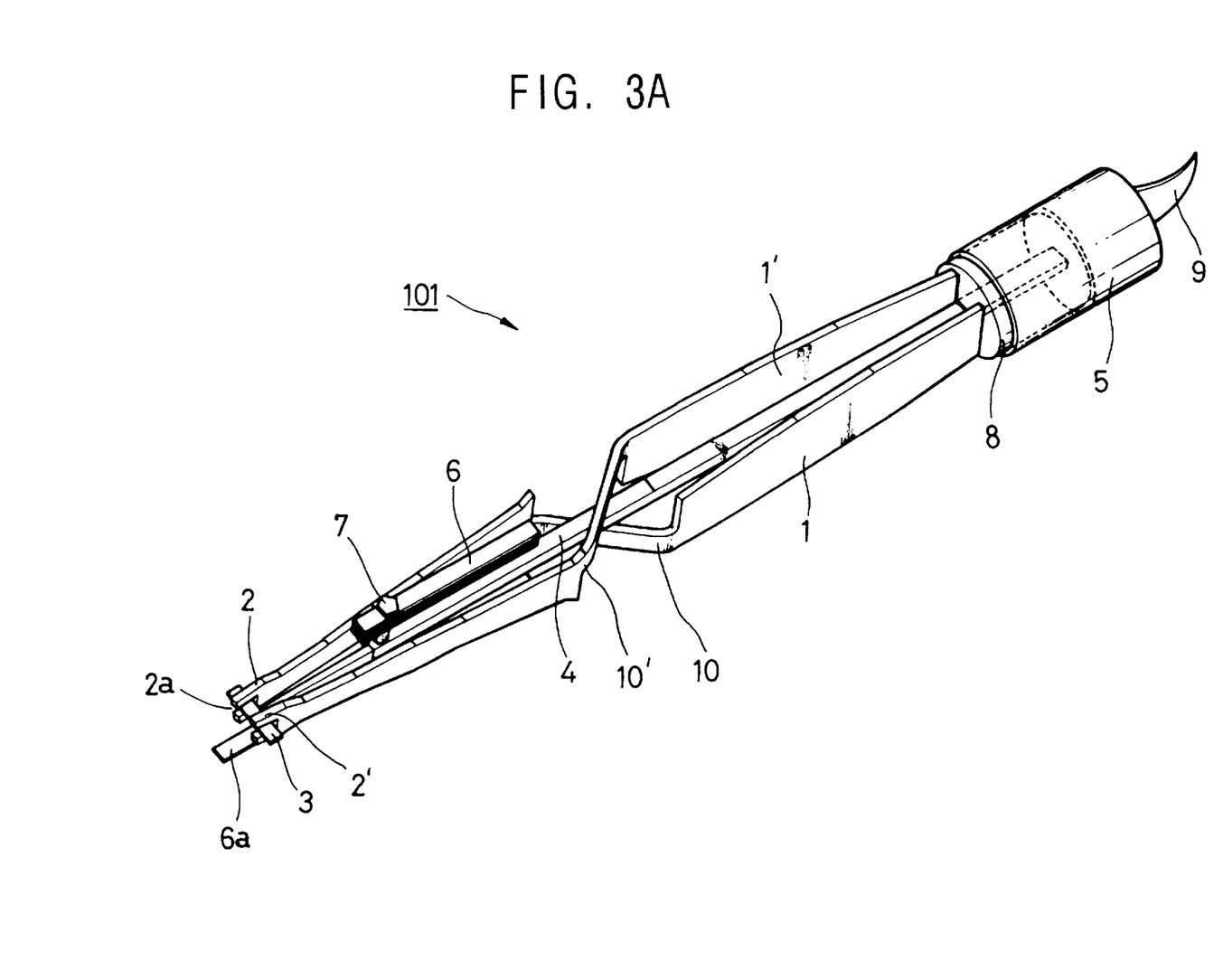
FIG. 3A is a perspective view of a first embodiment of the inventive tweezer for holding an anterior bracket and measuring distance.
Figure 4A:
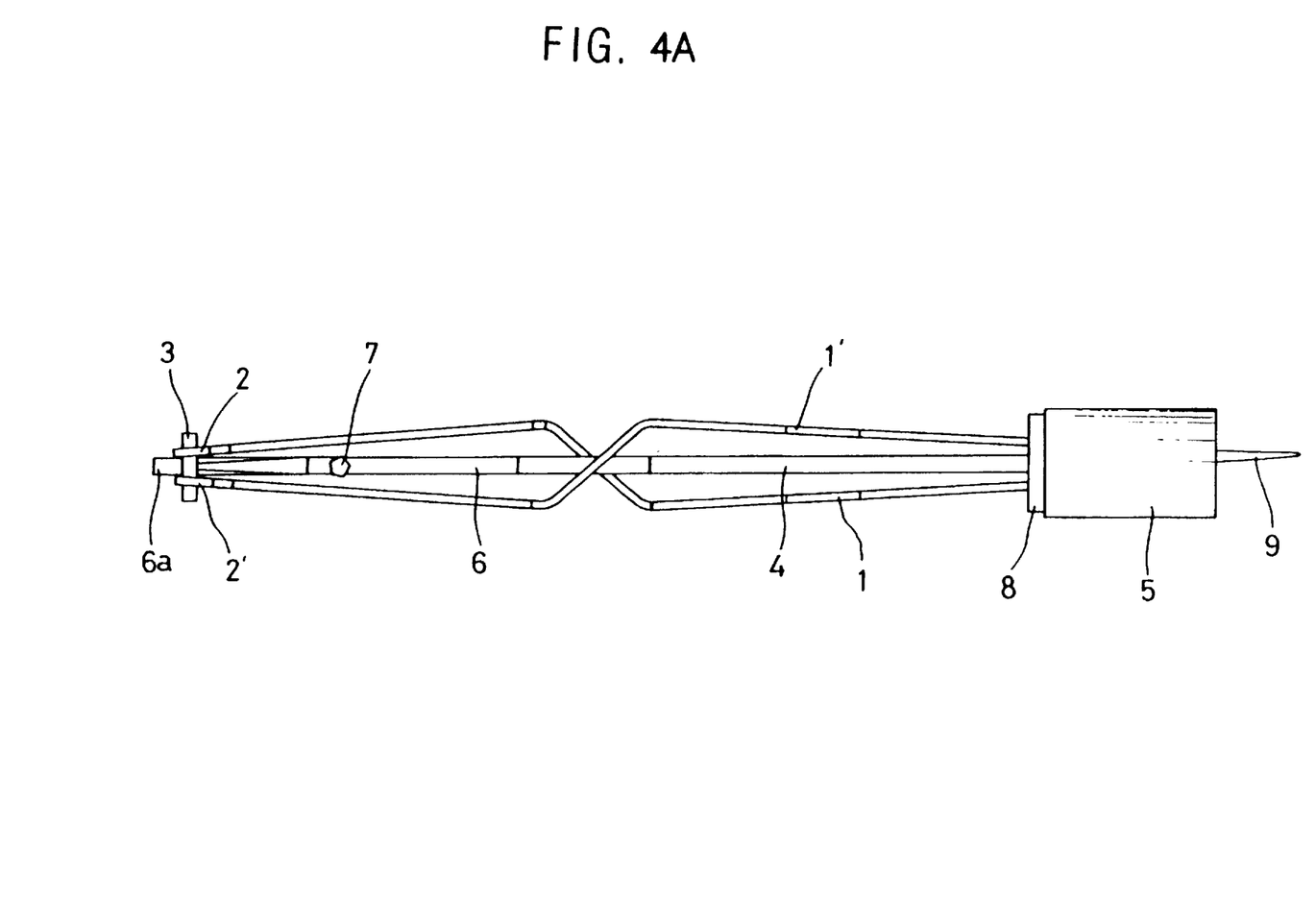
FIG. 4A is a top plan view of the first embodiment of the inventive tweezer for holding an anterior bracket and measuring distance.
Figure 4B:
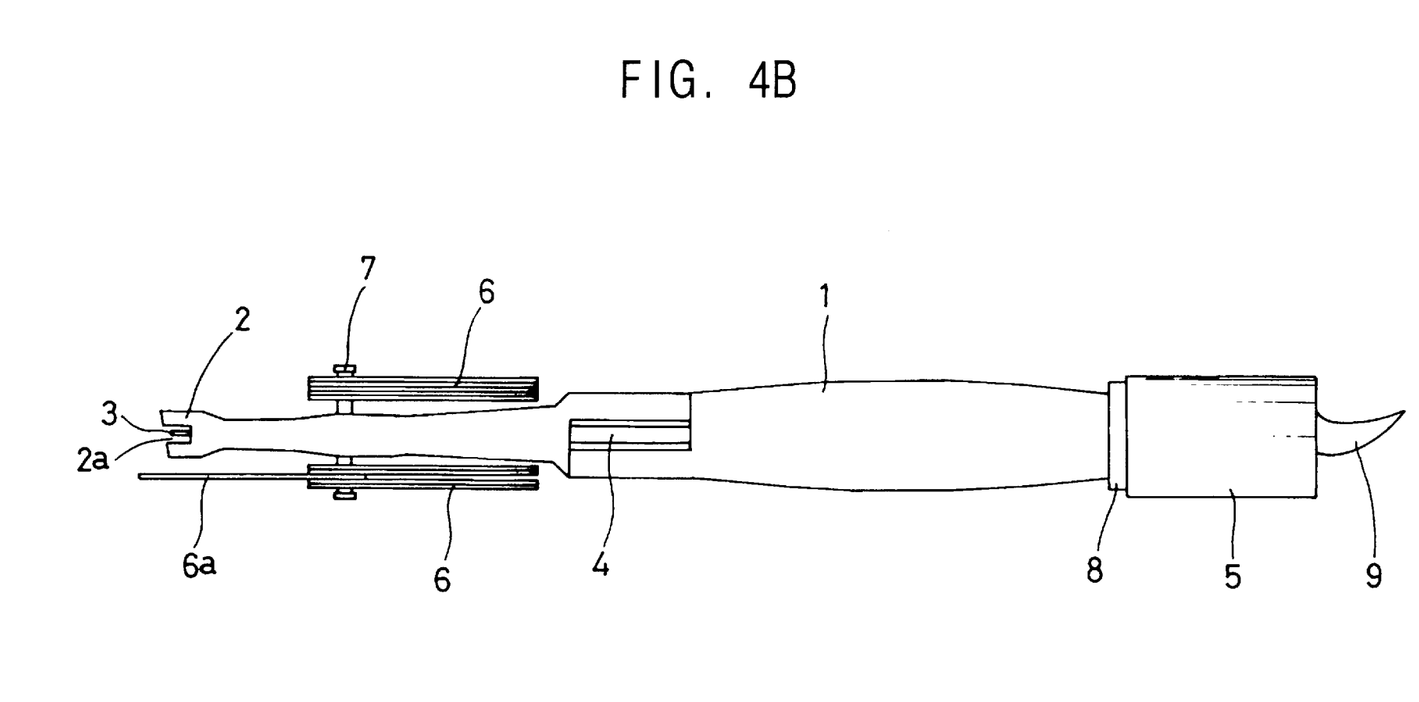
FIG. 4B is a side view of the first embodiment of the inventive tweezer for holding an anterior bracket and measuring distance.

As can be seen in FIG. 3A, FIG. 4A and FIG. 4B, tweezers for attaching an anterior bracket are comprised of two members 1 and 1' having two end parts each, preferably made of a strong and durable material such as stainless steel, although other materials could be used. The first end parts of members 1 and 1' are associated with a holding part 8 having a cylindrical shape. Both members 1 and 1' are cranked in opposite directions at their cross-over section, where members 1 and 1' cross over each other to form the gripping mechanism. At this cross-over position, member 1 has a bottom notch 10 formed therein while member 1' has a top notch 10' in a manner such that there is sufficient clearance for member 1 to cross over member 1' at the location of notches 10 and 10'. This relationship between notches 10 and 10' can be seen most clearly in FIG. 3A. It is to be understood, however, that the notches 10 and 10' are not crucial to the present invention, as other shapes and sizes of the notches could also be used.

There are gripping jaws 2 and 2' at the second end parts of the members 1 and 1' to grip the tie wings of an orthodontic bracket. Each of the gripping jaws 2 and 2' have a groove 2a at the central section of its front edge to enable turning or replacement of an adjustment plate 3 which will be described in detail below. Also, their front edges are cutting surfaces that are equally inclined to a vertical axis.

An outer rim 5, associated with the holding part 8, rotates an adjustment shaft 4 which extends along the longitudinal direction of the tweezers 101 and is positioned between the members 1 and 1'.

Figure 7:
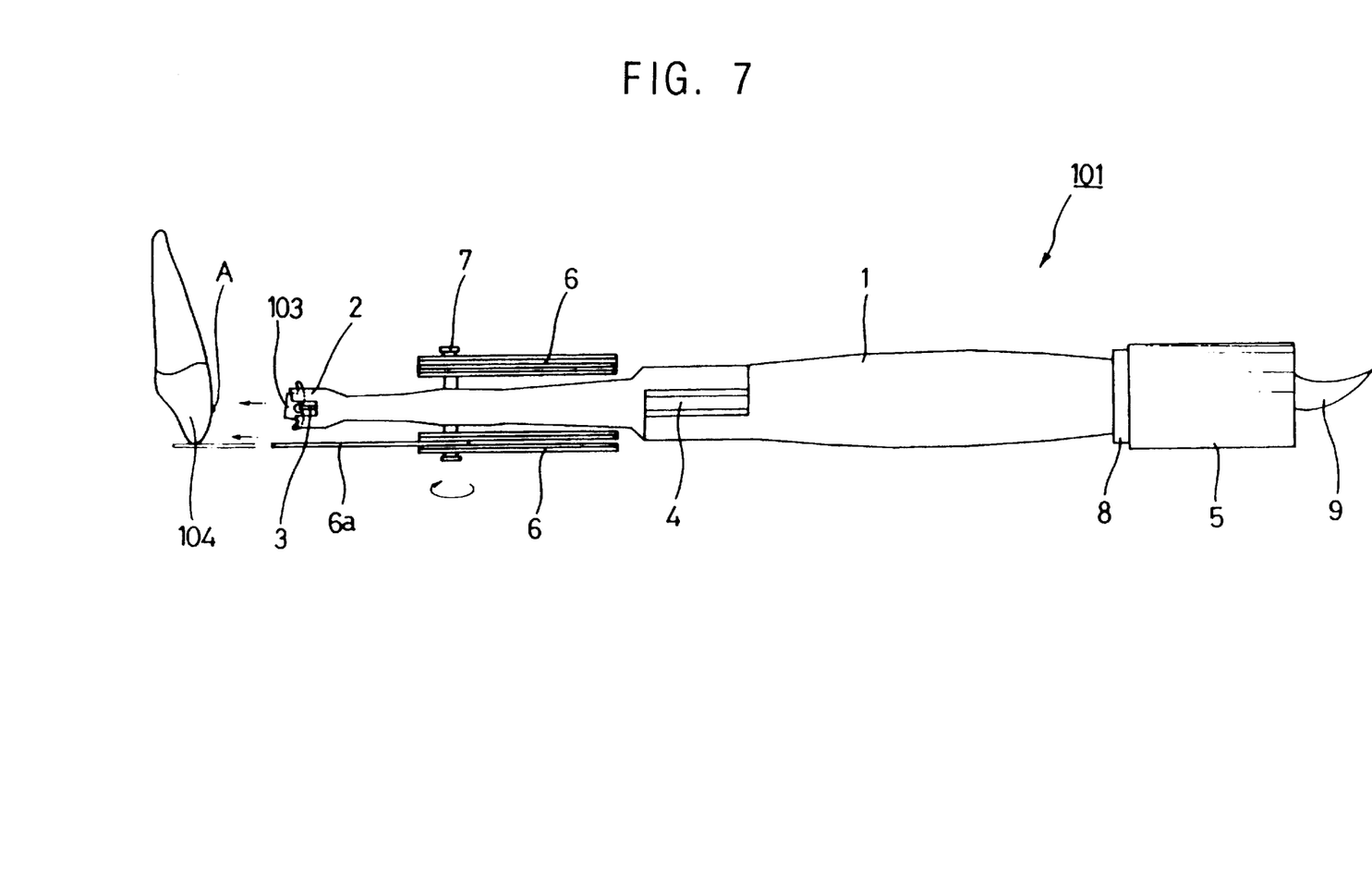
FIG. 7 is a side view of the first embodiment of the inventive tweezer for holding an anterior bracket and measuring distance as it would be used by an orthodontist to attach an anterior bracket to a patient's tooth.

As more clearly shown in FIG. 3A, the adjustment shaft 4 has two end portions. One end portion extends through the holding part 8 and is associated with the outer rim 5, and the other end portion is positioned between the gripping jaws 2 and 2' and is integrally associated with the adjustment plate 3 in order to adjust the bracket. The adjustment plate 3, having a flat surface, is located in the groove 2a. As shown in FIG. 1 and FIG. 7, when the tweezers 101 grip the orthodontic bracket 103, the adjustment plate 3 is inserted into the slot 32a which is variously angled to the horizontal center line of the bracket 103. Therefore, the adjustment plate 3 is rotated in unison with the adjustment shaft 4 in order to accurately adjust the position of the bracket 103. Also, the adjustment plate 3 forms a reference point which enables the user to measure distance between the end of tooth and the slot 32a of the bracket 103.

A gauge 6 is comprised of a number of plates 6a which have a predetermined thickness and are stacked on each other, and a pivoting shaft 7 which is associated with the adjustment shaft 4. The pivoting shaft 7 enables each plate 6a to pivotally fold and unfold. The stacked plates 6a are in total 1 mm~2.5 mm thick and are associated with the bottom and/or top of the adjustment shaft 4 by means of the pivoting shaft 7. Each plate 6a is approximately 3.5 mm~5.5 mm away from the adjustment plate 3.

Therefore, when an orthodontist wants to accurately attach the bracket 103 to a tooth's surface 104, he can select and unfold one of the plates 6a of the gauge 6 in accordance with the size and shape of the tooth and thereby attach the bracket 103 accurately to an attaching position on the tooth. The plates 6A and guage 6 are used to adjust for distance between the end of tooth and the slot 32a and referring to the vertical scribe line (not shown) which is the reference line to ascertain whether or not the vertical axis of the bracket 103 is parallel to the vertical axis of the tooth.

Figure 3B:
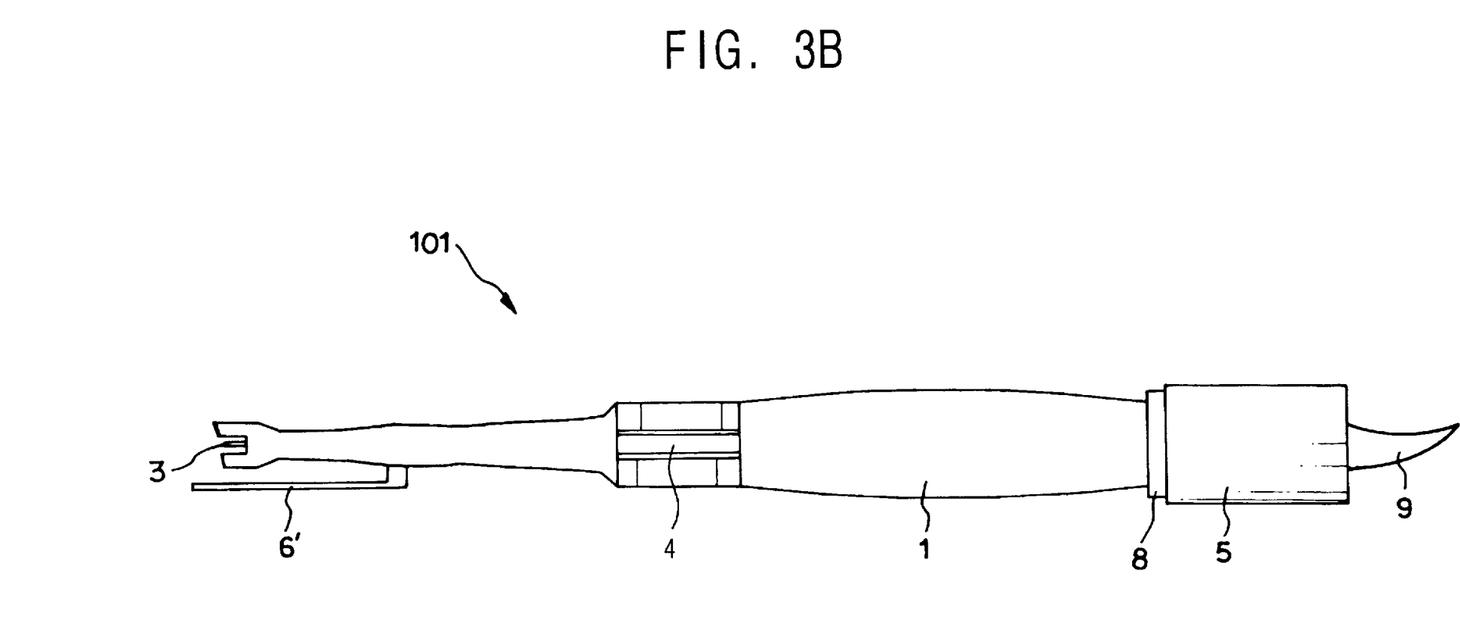
FIG. 3B is a perspective view of a second embodiment of the inventive tweezer for holding an anterior bracket and measuring distance.

Also, as can be seen in FIG. 3B, to uniformly maintain distance between the adjustment plate 3 and a gauge, the gauge 6' in the second embodiment of the invention is divided by the cranking into two regions which are parallel to each other and angled twice with opposite orientation in the longitudinal direction. One region is connected with the adjustment shaft 4 and the other region cames into contact with the end of tooth and is parallel to the adjustment shaft 4. The gauge may, of course, not only be of U-shaped configuration in the longitudinal direction but may also be cranked in a wide variety of embodiments not shown.

A knife 9 is formed at the other end portion of the adjustment shaft 4 which extends through the outer rim 5 and has a crescent shaped configuration. The shape of the knife is, of course, only exemplary and may be differently designed in accordance with the purpose for which they are intended. The knife 9 is used for removing bond material and debris which remains on the tooth surface after attaching the bracket to the patient's tooth.

Figure 5A:
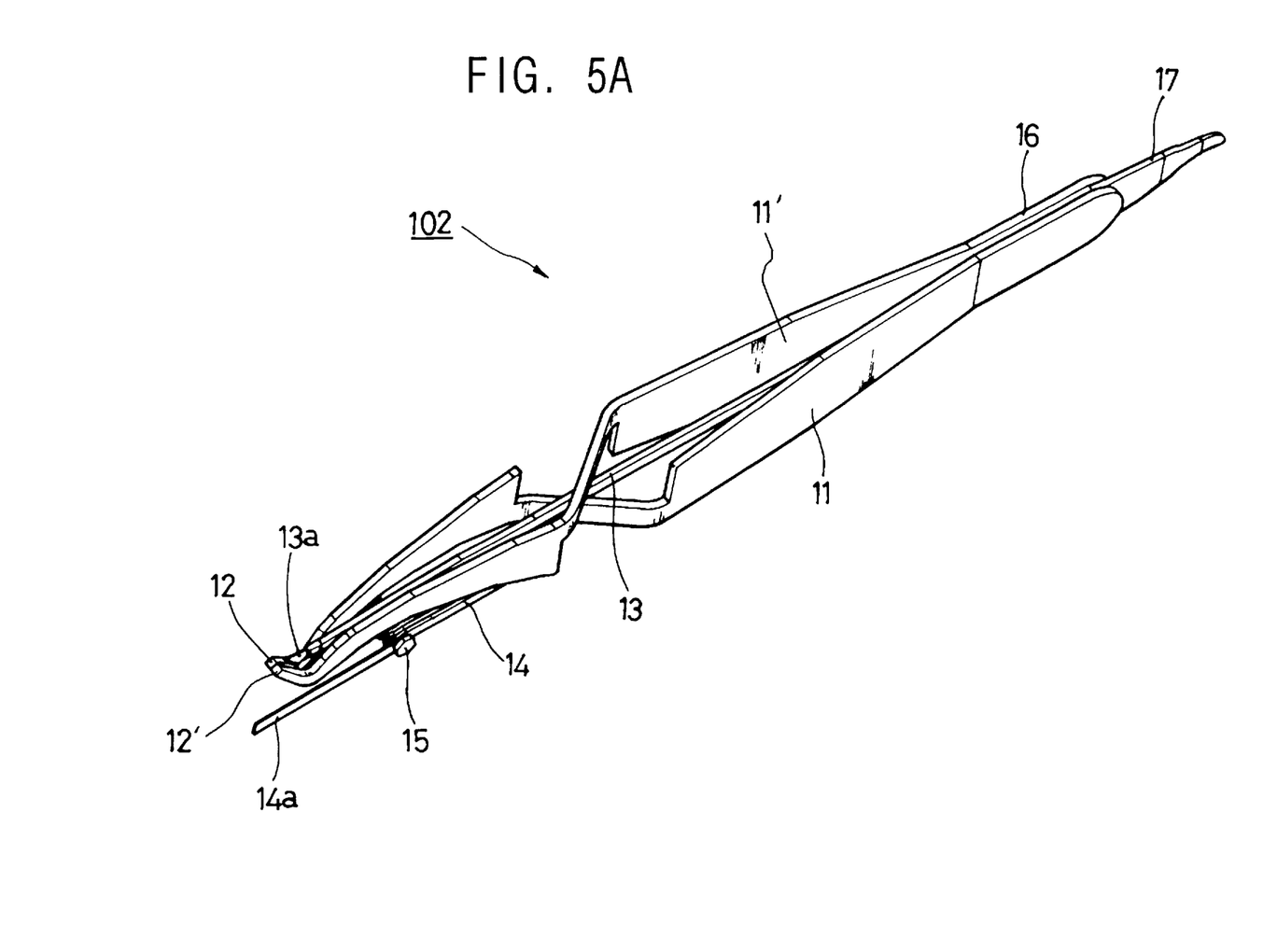
FIG. 5A is a perspective view of a third embodiment of the inventive tweezer for holding a posterior bracket and measuring distance.
Figure 6A:
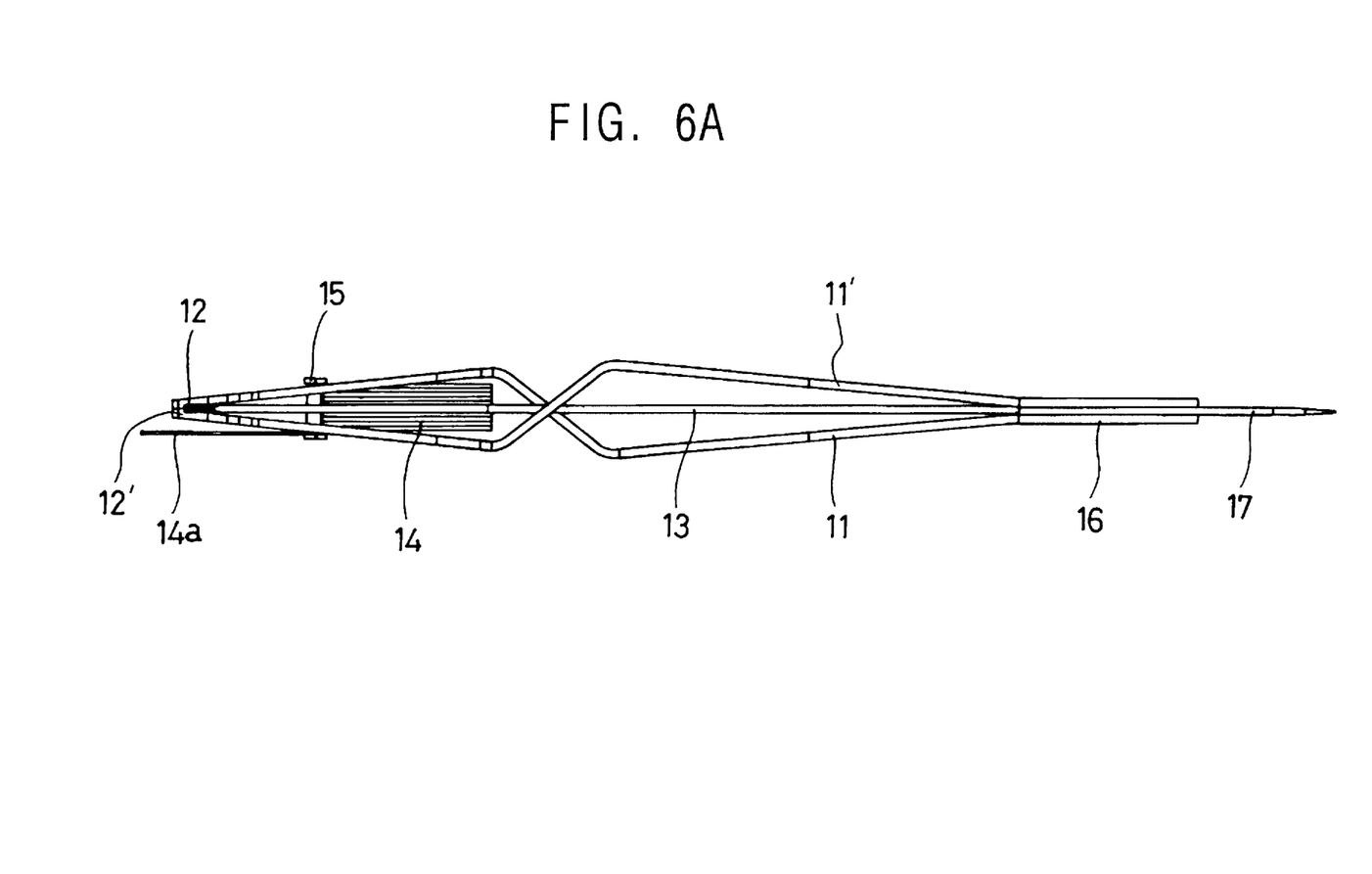
FIG. 6A is a top plan view of the third embodiment of the inventive tweezer for holding a posterior bracket and measuring distance.
Figure 6B:
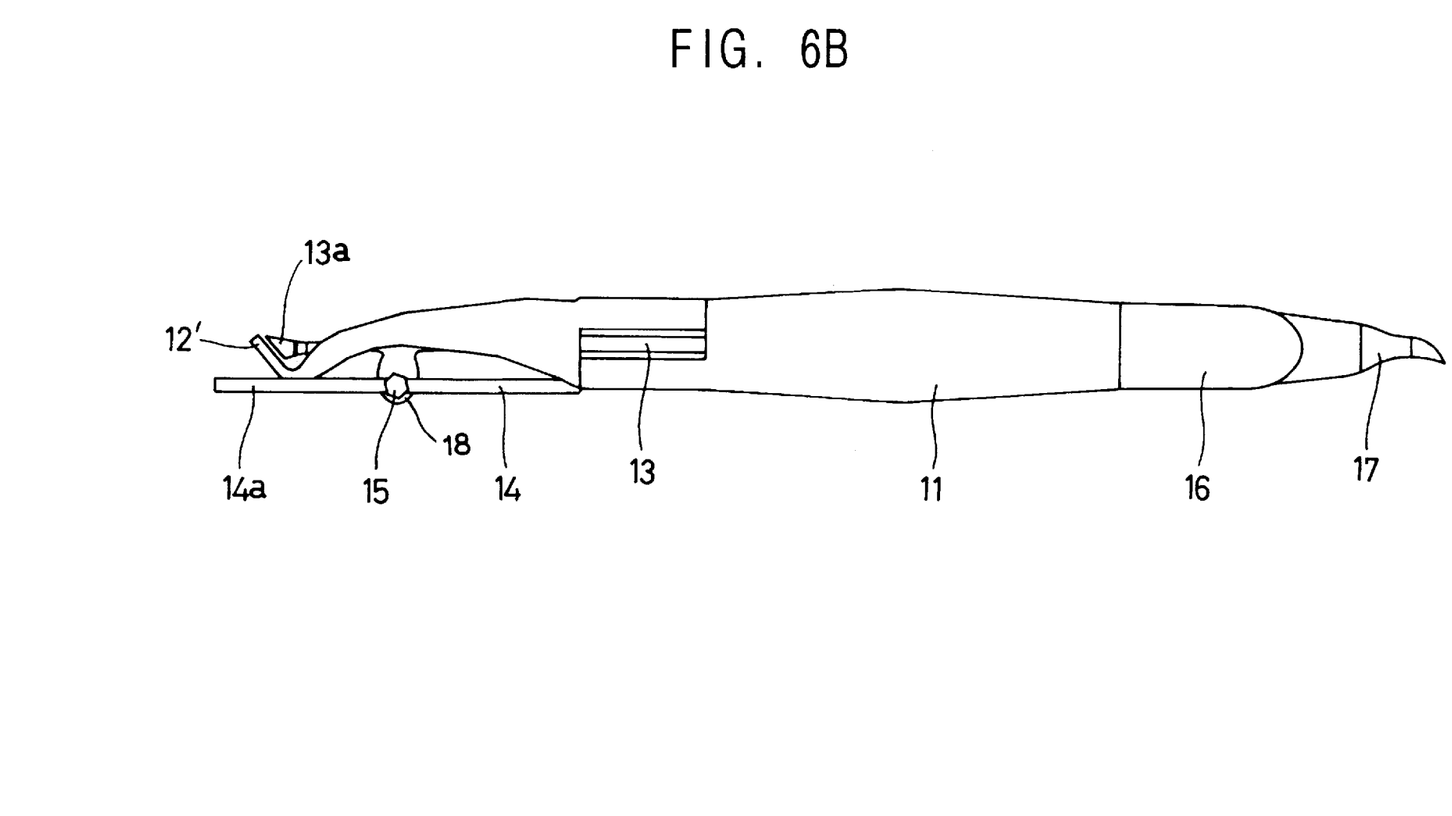
FIG. 6B is a side view of the third embodiment of the inventive tweezer for holding a posterior bracket and measuring distance.

As can be seen in FIG. 5A, FIG. 6A and FIG. 6B, tweezers for attaching an posterior bracket are also comprised of two members 11 and 11' having two end parts, preferably made of a strong and durable material such as stainless steel, although other materials could be used. The first end parts 16 of members 11 and 11' are associated with an adjustment shaft 13. Both members 11 and 11' are securely connected to each other until the bend, where both members 11 and 11' are bent in opposite directions so that they move away from each other for a set distance. Also, they are cranked in opposite directions at their cross-over section, where members 11 and 11' cross over each other to form the gripping mechanism. At this cross-over position, member 11 has a bottom notch 10 formed therein while member 11' has a top notch 10' in a manner such that there is sufficient clearance for member 11 to cross over member 11' at the location of notches 10 and 10'. This relationship between notches 10 and 10' can be seen most clearly in FIG. 5A. It is to be understood, however, that the notches 10 and 10' are not crucial to the present invention, as other shapes and sizes of the notches could also be used.

Figure 8:
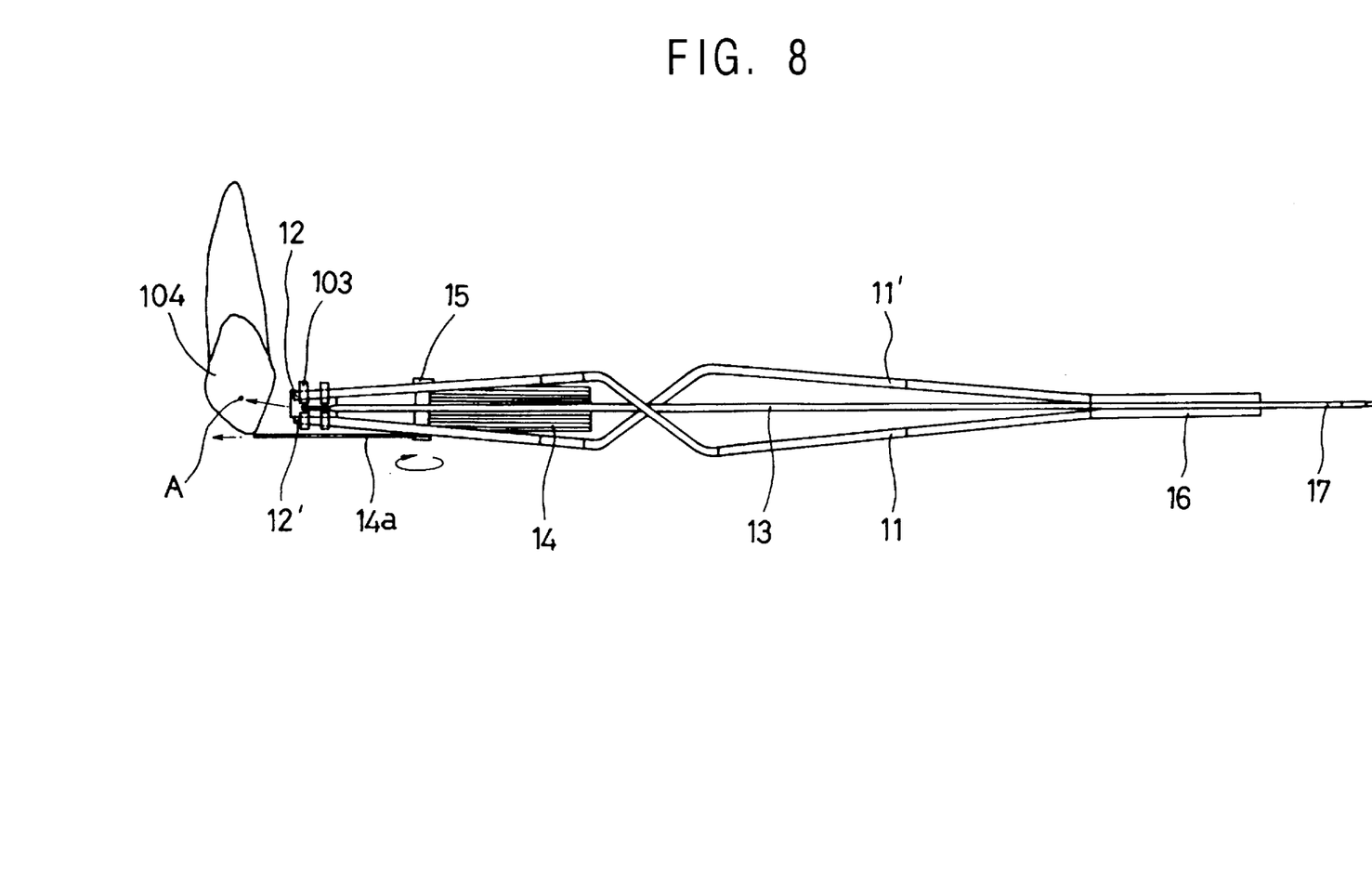
FIG. 8 is a top plan view of the third embodiment of the inventive tweezer for holding a posterior bracket and measuring distance as it would be used by an orthodontist to attach a posterior bracket a patient's tooth.

As more clearly shown in FIG. 2B and FIG. 8, the gripping jaws 12 and 12' at the second end parts of members 11 and 11' to are used to grip the stem of an orthodontic bracket. Each of the gripping jaws 12 and 12' have an upward bent portion at its other end. Also, the front edge of the gripping jaws 12 and 12' are slightly inclined to the vertical axis.

The adjustment shaft 13 extends along the longitudinal direction of the tweezers 102 and is positioned between the members 11 and 11'.

As more clearly shown in FIG. 5A, the adjustment shaft 13 has two end portions. One end portion forms a knife 17, which extends through the members 11 and 11', and the other end portion is positioned between the gripping jaws 12 and 12', forming the adjustment plate 13a in order to adjust the bracket. The adjustment plate 13a having a flat surface extends to the upward bent portions of the gripping jaws 12 and 12'. The sides of the gripping jaws 12 and 12' are parallel to the surface of the adjustment plate 13a.

As shown in FIG. 1 and FIG. 8, when the tweezers 101 grip the stem 36 of the orthodontic bracket 103, the adjustment plate 13a is inserted into the slot 32a which is variously angled to the horizontal center line of the bracket 103. Therefore, the adjustment plate 13a accurately adjusts the position of the bracket 103, which is held in the gripping jaws 12 and 12'. Also, the adjustment plate 13a forms a reference point which enables the user to measure distance between the end of a tooth and the slot 32a of the bracket 103.

A gauge 14 is comprised of a number of plates 14a which have a predetermined thickness and are stacked on each other, and a pivoting shaft 15 which is associated with the adjustment shaft 13. The pivoting shaft 15 enables each plate 14a to pivotally fold and unfold. The stacked plates 14a are in total 1 mm~2.5 mm thick and are associated with the left and/or right side of the adjustment shaft 13 by the pivoting shaft 15. Each plate 14a is approximately 3.5 mm~5.5 mm away from the adjustment plate 13a.

Therefore, when an orthodontist wants to accurately attach the bracket 103 to a tooth's surface 104, he/she can select and unfold one of the plates 14a of the gauge 14 in accordance with the size and shape of the tooth and thereby attach the bracket 103 accurately to an attaching position on the tooth. The plates 14a and guage 14 are used to adjust for distance between the end of tooth and the slot 32a and to refer to the vertical scribe line (not shown) which is the reference line to ascertain whether or not the vertical axis of the bracket 103 is parallel to the vertical axis of the tooth.

Figure 5B:
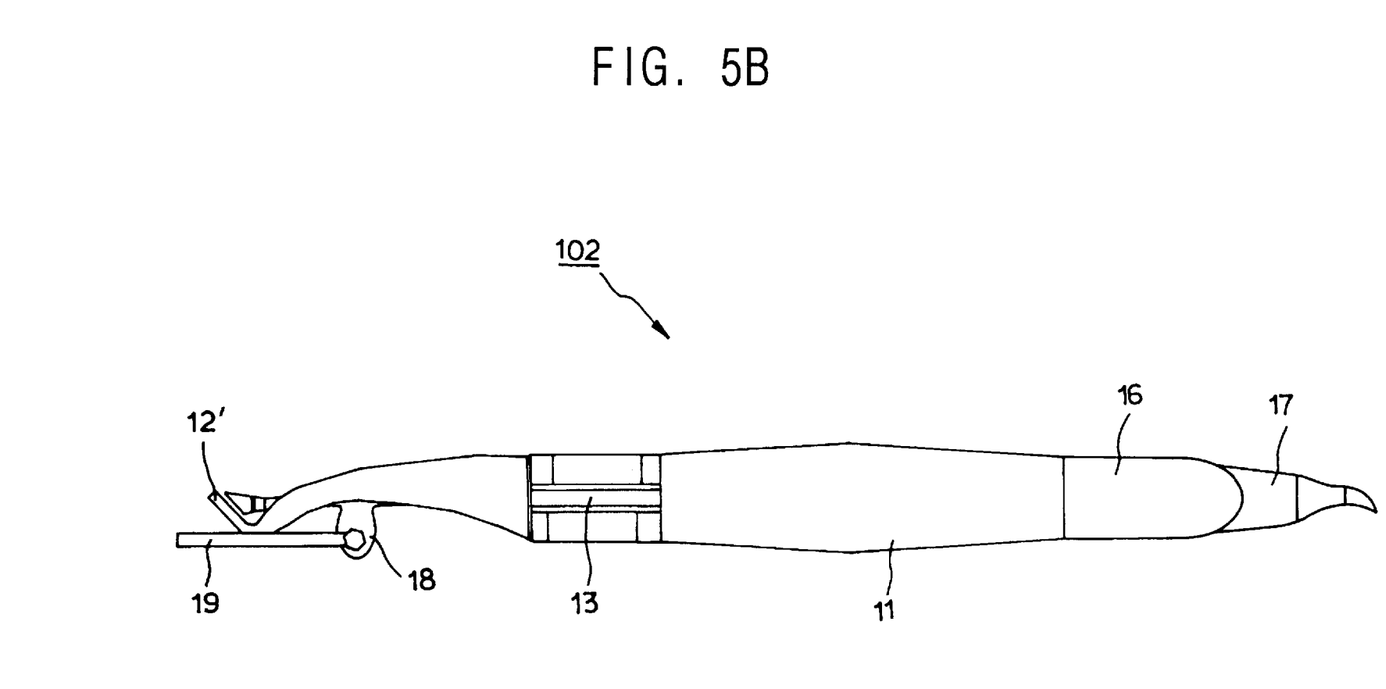
FIG. 5B is a perspective view of a fourth embodiment of the inventive tweezer for holding a posterior bracket and measuring distance.

Also, as can be seen in FIG. 5B, to uniformly maintain distance between the adjustment plate 13a and a gauge, the gauge 14' in the fourth embodiment of the invention is divided by the cranking into two regions which are parallel to each other and angled twice with opposite orientation in the longitudinal direction. One region is connected with the adjustment shaft 13 and the other region comes into contact with the end of a tooth and is parallel to the adjustment shaft 13. The gauge may, of course, not only be of U-shaped bent configuration in the longitudinal direction but also be cranked in a wide variety of embodiments not shown.

The knife 17 has a crescent shaped configuration. The shape of the knife is, of course, only exemplary and may be differently designed in accordance with the purpose for which they are intended. The knife 17 is used for removing bond material and debris which remains on the tooth surface after attaching the bracket to the patient's tooth.

What is claimed is:

1. Tweezers for adjusting an orthodontic bracket, said bracket having a slot, said tweezers comprising:

a pair of generally flat elongated members placed in an adjacent lengthwise relationship with one another, each of said members having a first end part and a second end part, said second end part forming a gripping jaw having a front edge provided with a central section and a groove at said central section;

means for adjusting the bracket positioned between said members and extending along a longitudinal direction of said tweezers, said means for adjusting the bracket including a first end portion connected with said first end part and a second end portion formed as an adjustment plate extending along said groove of said gripping jaw for accurately adjusting the position of the bracket and forming a reference point to measure distance when said adjustment plate is inserted into said slot of the bracket; and means for measuring distance between the end of a tooth and said slot of the bracket, said means for measuring the distance including a pivoting shaft and a number of plates which are stacked next to each other on said shaft and associated with at least one surface of said means for adjusting the bracket.

2. Tweezers according to claim 1, wherein said stacked plates are in total 1 mm~2.5 mm thick and each of said stacked plates is 3.5 mm~5.5 mm away from said adjustment plate.

3. Tweezers according to claim 1, wherein said means for measuring distance consists of a plate being of U-shaped configuration in the longitudinal direction, said U-shaped plate having two regions in parallel with said means for adjusting the bracket, one said region connected with said first end portion and said other region coming into contact with the end of a tooth.

4. Tweezers according to claim 1, wherein said means for measuring distance consists of a plate being angled twice with opposite orientation in the longitudinal direction, said plate having two regions in parallel with said means for adjusting the bracket, one said region connected with said first end portion and said other region coming into contact with the end of a tooth.

5. Tweezers according to claim 1, wherein each of said gripping jaws has a side, in which each of said gripping jaws has an upward bent portion and said adjustment plate is parallel to said side of said gripping jaws.

6. Tweezers according to claim 1, in which said front edge of each said gripping jaw is angled to the vertical axis.

7. Tweezers according to claim 1, in which said means for adjusting the bracket has a knife at said second end portion.

8. Tweezers according to claim 1, further comprising:

a holding part which associates each of said first end parts of said members with said second end portion of said means for adjusting the bracket; and an outer rim associated with said holding part in order to rotate said means for adjusting, said second end portion extending through said outer rim.

* * * * *